United States Patent [19]
Back et al.

[11] Patent Number: 5,733,295
[45] Date of Patent: Mar. 31, 1998

[54] SURGICAL VASCULAR CLIP

[75] Inventors: Lothar Back, Inzighofen; Gebhard Herrmann, Irndorf; Markus Nesper, Tuttlingen; Dieter Weisshaupt, Immendingen, all of Germany

[73] Assignee: Aesculap AG, Tuttlingen, Germany

[21] Appl. No.: 711,849

[22] Filed: Sep. 10, 1996

[30] Foreign Application Priority Data

Sep. 15, 1995 [DE] Germany .......................... 195 34 322.0

[51] Int. Cl.⁶ .................................................. A61B 17/08
[52] U.S. Cl. ...................... 606/158; 606/151; 606/157; 606/142; 606/143
[58] Field of Search ........................ 606/158, 157, 606/151, 143, 142; 24/437, 489, 497, 498, 513, 515, 516, 537, 545, 546, 555

[56] References Cited

U.S. PATENT DOCUMENTS

| | | | |
|---|---|---|---|
| 280,464 | 7/1883 | Gifford | 24/537 |
| 406,021 | 7/1889 | Bley | 24/537 |
| 2,042,891 | 6/1936 | Gailey | 24/537 |
| 5,366,459 | 11/1994 | Yoon . | |
| 5,388,313 | 2/1995 | Cameron | 24/537 |
| 5,520,701 | 5/1996 | Lerch | 606/151 |

FOREIGN PATENT DOCUMENTS

| | | | |
|---|---|---|---|
| 20981 | 1/1936 | Australia | 24/537 |
| 43 19 829 | 8/1994 | Germany . | |
| 44143 | 6/1927 | Norway | 24/515 |
| 2124501 | 2/1984 | United Kingdom | 606/158 |

*Primary Examiner*—Michael Buiz
*Assistant Examiner*—Tina T. D. Pham
*Attorney, Agent, or Firm*—Barry R. Lipsitz; Ralph F. Hoppin

[57] ABSTRACT

To facilitate the production of a surgical vascular clip having two arms with clamping jaws, the arms being resiliently pressable against each other and meeting at an end section of the clip, and also having a tensioning section adjoining the end section in the direction towards the clamping jaws and being surrounded by a ring displaceable in the longitudinal direction of the tensioning section, it is proposed that the arms with the clamping jaws, the tensioning section and the end section be designed as a one-piece component.

21 Claims, 1 Drawing Sheet

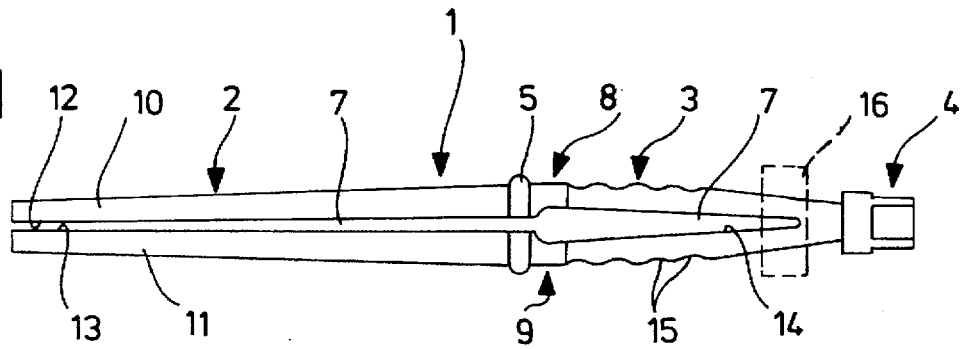
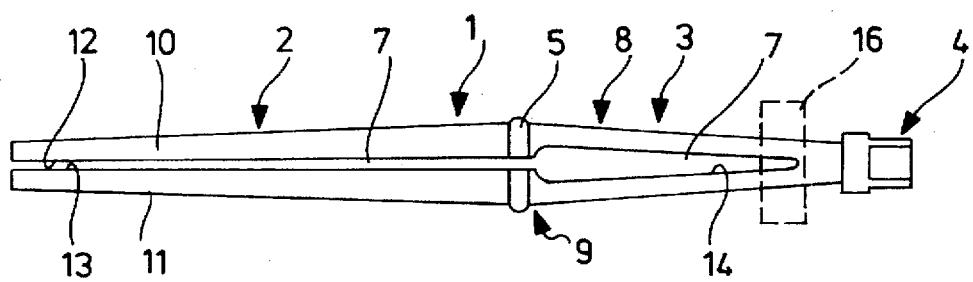
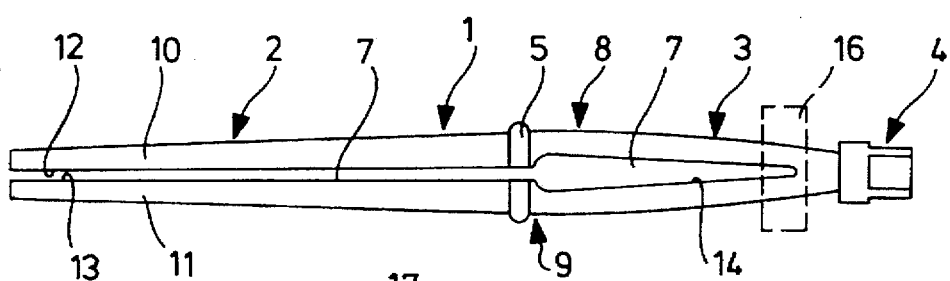
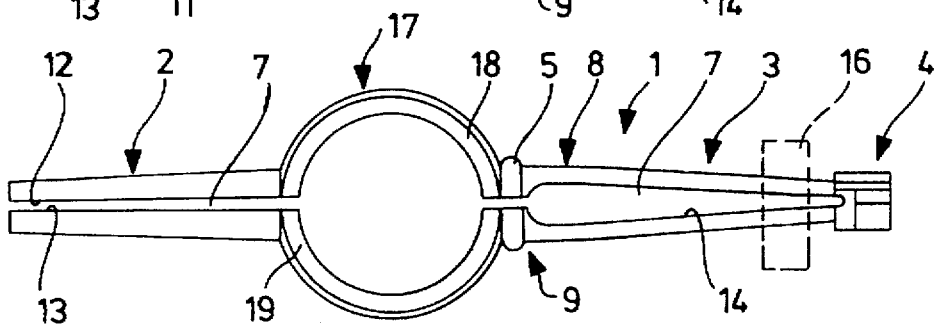
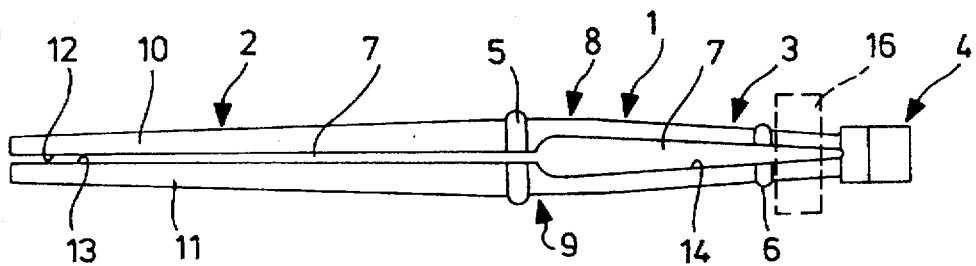

SURGICAL VASCULAR CLIP

BACKGROUND OF THE INVENTION

The invention relates to a surgical vascular clip having two arms with clamping jaws, the arms being resiliently pressable against each other and meeting at an end section of the clip, and also having a tensioning section adjoining the end section in the direction towards the clamping jaws and being surrounded by a ring displaceable in the longitudinal direction of the tensioning section.

Such surgical clips are known, for example, from DE 43 19 829 C1. These clips can be applied with a special applicator to the parts of a vessel to be clamped, and the clip can be closed by displacement of the ring on the tensioning section.

Known clips consist of semicircular profiled rods which rest against one another in the area of the end section and have to be joined together there, for example, by welding or pressing. As these clips are very small parts such a joining operation is difficult to perform.

The object of the invention is to so design a surgical clip of the generic kind that the production of the clips can be simplified.

SUMMARY OF THE INVENTION

This object is accomplished in accordance with the invention with a surgical clip of the kind described at the outset by the arms with the clamping jaws, the tensioning section and the end section being designed as a one-piece component. Joining of these parts is thereby dispensed with.

In surgical suture instruments, i.e., devices for making a suture-like joint, it is known per se to design two-armed connecting elements with a longitudinally displaceable ring as one piece. However, these are all parts which are to engage one another in the fashion of a loop-shaped suture joint, i.e., they have no clamping function whatever, as is required with a surgical clip. In particular with a surgical vascular clip, it is necessary for high clamping forces to be applied, and it must, therefore, be ensured that the clamping jaws will be pressed against each other under high clamping force for a long time. Therefore, such surgical vascular clips are not comparable with suture devices of the kind explained above (U.S. Pat. No. 5,366,459).

It is expedient for the end section to have the shape of a circular cylinder which projects in the form of a step over the adjoining tensioning section. This end section can be used to clamp the clip in an applicator so the applicator holds the clip reliably and is also able to displace the ring arranged on it.

It is favorable for the tensioning section to be closed off towards the clamping jaws by a projection which preferably has the shape of a shoulder surrounding the arms on the outside thereof. The displaceability of the ring on the tensioning section is delimited by such a projection, and, therefore, there is no danger that the ring will be displaced too far.

It is also possible for the tensioning section to be closed off towards the end section by a projection which also preferably has the shape of a shoulder surrounding the arms on the outside thereof. In this way, the displacement of the ring along the tensioning section is limited to the area between these projections. This proves particularly useful when the ring has projections protruding inwardly between the arms and bends the arms outwardly by means of these projections when it is pushed back. This outward bending is delimited towards the end section of the clip by the projection.

Provision may be made for the tensioning section to widen conically from the end section to the clamping jaws.

In another embodiment, provision is made for a cylindrical part to adjoin the conically widening part of the tensioning section. When the ring is pushed forward, the clip is closed increasingly in the conical part, but the tension is maintained in the cylindrical part and so, on the one hand, a certain tolerance for the displacement of the ring is achieved by displacement in this area, and, on the other hand, it is thus ensured that the ring does not slide back unintentionally into the open position.

In a further preferred embodiment, provision is made for the arms to be corrugated in the longitudinal direction in the area of the tensioning section, i.e., transverse ribs extend around the clip so the ring is held by this corrugation or these transverse ribs and prevented from sliding off along the tensioning section. In addition to this, the ring can have on its inner side projections which engage the corrugation or the ribs. This results in a stepped displacement of the ring along the tensioning section and hence in stepped generation of tension in the area of the clamping jaws, which thereby enables the operator to set different tension values in a precisely defined manner.

It is expedient for the arms to enclose between them in the tensioning section a gap whose width increases from the end section to the clamping jaws. Projections on the ring can engage in this gap and cause the clamping jaws to be spread open when the ring is pushed back.

It is also advantageous for the gap to have end surfaces at the clamping jaw end of the tensioning section which are oriented towards the other arm. The widening gap is thereby narrowed again towards the clamping jaws.

In a particularly preferred embodiment, provision is made for the arms to be bent outwardly in arcuate configuration between the clamping jaws and the tensioning section. An opening is thereby produced in the area between these, through which, for example, a vessel can extend. It is thus possible to also use the clip in areas in which there are parts of the body which are not to be clamped.

In a particularly preferred embodiment of the clip, provision is made for it to consist of an elongate cylindrical part which is divided into two arms by a longitudinal slit extending as far as the end section. During the manufacture, a cylindrical part is first produced, for example, on a lathe, and starting from the tip opposite the end section, this cylindrical part is divided by a longitudinal slit into two arms or legs. It is thus possible to produce a one-piece clip in a simple way without the necessity of complicated connections in the area of the end section.

It is advantageous for the longitudinal slit to have essentially a constant width in the area of the clamping jaws, to widen on entering the tensioning section and to decrease in width again in the direction towards the end section. When the clamping jaws are bent together, they will approach each other on account of the one-piece connection in the area of the end section such that they first touch at the free end and then come to rest against each other continuously from the front to the rear. This ensures that the clamping jaws do not gape open towards the front, but are always reliably closed. This effect can be reinforced by the slit in the area of the clamping jaws widening slightly in the direction towards the end section.

The longitudinal slit can be produced with particular advantage with a wire eroding machine. However, other processes, for example, using an electron beam or separating by means of a laser beam, may also be used.

In a clip with arms bent outwardly in arcuate configuration, provision may be made for the areas of the arms bent outwardly in arcuate configuration to be formed from a convex thickening of the cylindrical part by flattening on both sides and by convex widening of the longitudinal slit. Starting from a cylindrical part, this is produced with a convex thickening, for example, a spherical thickening, which is subsequently flattened off on both sides, for example, by milling, and in the resulting disc-shaped area of the cylindrical part, the longitudinal slit is convexly widened so that the contour of the longitudinal slit extends essentially parallel to the outer contour of the disc. Arcuate arm sections can thus be produced to create the desired window area.

The following description of preferred embodiments of the invention serves in conjunction with the appended drawings to explain the invention in greater detail.

BRIEF DESCRIPTION OF THE DRAWINGS

FIG. 1 a clip with a corrugated, conical tensioning section;

FIG. 2 a clip with a smooth, conical tensioning section;

FIG. 3 a clip with a tensioning section having conical and cylindrical areas;

FIG. 4 a clip with arcuately bent arms forming a window; and

FIG. 5 a clip with a shoulder-shaped projection for delimiting the tensioning section at the end section side.

DETAILED DESCRIPTION OF THE INVENTION

All clips 1 illustrated in FIGS. 1 to 5 are produced as elongate cylindrical parts, for example, on a lathe. These cylindrical parts comprise a clamping section 2 which widens conically to a slight extent, an adjoining tensioning section 3 whose outer diameter decreases, and a cylindrical end section 4 which projects in the form of a step relative to the tensioning section 3. The end section 4 can be designed as a solid cylinder or as a sleeve-shaped cylinder which is open towards the rear and can be optionally provided with a stepped recess.

In all embodiments, a projection in the form of a ring-shaped shoulder 5 surrounding the cylindrical part is provided between the clamping section 2 and the tensioning section 3. In a preferred embodiment (FIG. 5), a further ring-shaped shoulder 6 can also be provided in the rear part of the tensioning section 3 in the proximity of the end section 4.

In all cases, this cylindrical part is divided by a longitudinal slit 7 into two arms 8, 9, which are integrally connected to each other in the area of the end section 4. In the clamping section 2, this longitudinal slit 7 has a constant and slight width so the clamping section 2 is divided into two clamping jaws 10, 11 which lie opposite each other with plane clamping surfaces 12, 13. These clamping surfaces 12, 13 can have a profile, for example, an embossing.

The longitudinal slit 7 widens as it enters the tensioning section 3 and narrows in the direction towards the end section 4, thereby producing a wedge-shaped space 14 in the area of the tensioning section 3.

The longitudinal slit 7 can be made by various processes. It can be produced with particular advantage in a wire-eroding process or by a process using a beam, for example, an electron beam or a laser beam. A longitudinal slit 7 with a certain contour can be cut in the cylindrical part by all these processes.

Different outer contours are possible in the area of the tensioning section 3. In the embodiment of FIG. 2, the outer contour in this area is conical throughout the entire length of this area. In the embodiment of FIG. 3, a cylindrical part adjoins the conical part of the tensioning section. In the embodiment of FIG. 1, the tensioning section is also of conical design, but, in addition, the outer contour is of corrugated shape in the longitudinal direction, which produces ribs 15 extending in the circumferential direction.

With all clips 1, a ring 16 is placed on the tensioning section 3. The ring 16 surrounds the two arms 8, 9 and is displaceable along the tensioning section 3. This ring 16 is designed as a separate part and is placed over the ring-shaped shoulder 5 by, for example, pressing the arms 8, 9 together. This ring can carry inwardly protruding projections which engage the wedge-shaped space 14 and spread open the arms 8, 9 when the ring is pushed back. When the ring is pushed forward, it presses the two arms 8 and 9 together elastically and thereby presses the clamping surfaces 12, 13 against each other.

In the embodiment of FIG. 4, a window section 17 is also arranged between the clamping jaws 10, 11, on the one hand, and the tensioning section 3, on the other hand. In this area, the arms 8, 9 are of outwardly curved configuration and thereby enclose a window opening for receiving parts of tissue which are not clamped together.

These curved arm sections 18, 19 can also be produced starting from a cylindrical part. The cylindrical part is provided with a spherical thickening in the area of the window section 17. This thickening is then flattened from two sides, for example, by milling, and, in particular, perpendicularly to the plane of the longitudinal slit 7. The spherical thickening is thus reduced to a disc-shaped thickening. In the area of this disc-shaped thickening, the longitudinal slit 7 is then widened in the shape of a circle so only the arcuate arm sections 18 and 19 remain.

In spite of this very complicated clip configuration, it is thus possible to produce a one-piece clip wherein complicated joining techniques can be avoided.

What is claimed is:

1. A surgical vascular clip, comprising:

two arms with clamping jaws;

said arms being resiliently pressable against each other and meeting at an end section of said clip, and also having a tensioning section adjoining said end section in the direction towards said clamping jaws and being surrounded by a ring displaceable in the longitudinal direction of said tensioning section, wherein:

said end section has the shape of a circular cylinder which projects in the form of a step over said adjoining tensioning section; and said tensioning section is closed off towards said clamping jaws by a projection.

2. A clip as defined in claim 1, wherein:

said projection has the shape of a shoulder surrounding said arms on the outside thereof.

3. A surgical vascular clip, comprising:

two arms with clamping jaws;

said arms being resiliently pressable against each other and meeting at an end section of said clip, and also having a tensioning section adjoining said end section in the direction towards said clamping jaws and being surrounded by a ring displaceable in the longitudinal direction of said tensioning section, wherein:

said arms with said clamping jaws, said tensioning section and said end section are designed as a one-piece component;

said tensioning section is closed off towards said clamping jaws by a projection;

said tensioning section widens conically from said end section to said clamping jaws; and said arms are defined by a longitudinal slit extending in said clip as far as said end section, where said slit has essentially a constant width in the area of said clamping jaws, widens on entering said tensioning section and decreases in width again in the direction towards said end section.

4. A clip as defined in claim 3, wherein:

said tensioning section is closed off towards said end section by a projection.

5. A clip as defined in claim 4, wherein:

said projection has the shape of a shoulder surrounding said arms on the outside thereof.

6. A clip as defined in claim 3, wherein:

a cylindrical part adjoins said conically widening part of said tensioning section.

7. A clip as defined in claim 3, wherein:

said arms are corrugated in the longitudinal direction in the area of said tensioning section.

8. A clip as defined in claim 3, wherein:

in said tensioning section, said arms enclose between them a gap, the width of which increases from said end section toward said clamping jaws.

9. A clip as defined in claim 8, wherein:

said gap has at the clamping jaw end of said tensioning section end surfaces which are oriented towards the other arm.

10. A clip as defined in claim 8, wherein:

it consists of an elongate cylindrical part which is divided into two arms by a longitudinal slit extending as far as said end section.

11. A clip as defined in claim 8, wherein:

said arms are defined by a longitudinal slit extending in said clip as far as said end section, where said slit has essentially a constant width in the area of said clamping jaws, widens on entering said tensioning section and decreases in width again in the direction towards said end section.

12. A clip as defined in claim 3, wherein:

in said tensioning section, said arms enclose between them a gap, the width of which increases from said end section toward said clamping jaws.

13. A clip as defined in claim 12, wherein:

said gap has at the clamping jaw end of said tensioning section end surfaces which are oriented towards the other arm.

14. A clip as defined in claim 3, wherein:

areas of said arms are bent outwardly in arcuate configuration between said clamping jaws and said tensioning section.

15. A clip as defined in claim 14, wherein:

said areas of said arms bent outwardly in arcuate configuration are formed from a convex thickening of said cylindrical part by flattening on both sides and by convex widening of said longitudinal slit.

16. A clip as defined in claim 3, wherein:

said clip is formed as an elongate cylindrical part.

17. A surgical vascular clip, comprising:

two arms with clamping jaws;

said arms being resiliently pressable against each other and meeting at an end section of said clip, and also having a tensioning section adjoining said end section in the direction towards said clamping jaws and being surrounded by a ring displaceable in the longitudinal direction of said tensioning section, wherein:

said arms with said clamping jaws, said tensioning section and said end section are designed as a one-piece component;

said tensioning section is closed off towards said clamping jaws by a projection; and said longitudinal slit has essentially a constant width in the area of said clamping jaws, widens on entering said tensioning section and decreases in width again in the direction towards said end section.

18. A surgical vascular clip, comprising:

two arms with clamping jaws;

said arms being resiliently pressable against each other and meeting at an end section of said clip, and also having a tensioning section adjoining said end section in the direction towards said clamping jaws and being surrounded by a ring displaceable in the longitudinal direction of said tensioning section, wherein:

said arms with said clamping jaws, said tensioning section and said end section are designed as a one-piece component;

said tensioning section widens conically from said end section to said clamping jaws; and a cylindrical part adjoins said conically widening part of said tensioning section.

19. A surgical vascular clip, comprising:

two arms with clamping jaws;

said arms being resiliently pressable against each other and meeting at an end section of said clip, and also having a tensioning section adjoining said end section in the direction towards said clamping jaws and being surrounded by a ring displaceable in the longitudinal direction of said tensioning section, wherein:

said arms with said clamping jaws, said tensioning section and said end section are designed as a one-piece component;

said tensioning section is closed off towards said clamping jaws by a projection;

said tensioning section widens conically from said end section to said clamping jaws; and a cylindrical part adjoins said conically widening part of said tensioning section.

20. A surgical vascular clip, comprising:

an elongate cylindrical part which is divided into two arms by a longitudinal slit extending as far as an end section of said clip;

said two arms having respective clamping jaws;

said arms being resiliently pressable against each other and meeting at the end section of said clip, and also having a tensioning section adjoining said end section in the direction towards said clamping jaws and being surrounded by a ring displaceable in the longitudinal direction of said tensioning section, wherein:

said arms with said clamping jaws, said tensioning section and said end section are designed as a one-piece component;

said tensioning section is closed off towards said clamping jaws by a projection;

said tensioning section widens conically from said end section to said clamping jaws; and in said tensioning section, said arms enclose between them a gap, the width of which increases from said end section toward said clamping jaws.

21. A surgical vascular clip, comprising:

two arms having respective clamping jaws;

said arms being resiliently pressable against each other and meeting at an end section of said clip, and also having a tensioning section adjoining said end section in the direction towards said clamping jaws and being surrounded by a ring displaceable in the longitudinal direction of said tensioning section, wherein:

said arms with said clamping jaws, said tensioning section and said end section are designed as a one-piece component;

said tensioning section is closed off towards said clamping jaws by a projection;

said tensioning section widens conically from said end section to said clamping jaws;

in said tensioning section, said arms enclose between them a gap, the width of which increases from said end section toward said clamping jaws; and said arms are defined by a longitudinal slit extending in said clip as far as said end section, where said slit has essentially a constant width in the area of said clamping jaws, widens on entering said tensioning section and decreases in width again in the direction towards said end section.

* * * * *